(12) United States Patent
Carmeli et al.

(10) Patent No.: US 10,534,813 B2
(45) Date of Patent: Jan. 14, 2020

(54) SIMPLIFIED VISUALIZATION AND RELEVANCY ASSESSMENT OF BIOLOGICAL PATHWAYS

(71) Applicant: International Business Machines Corporation, Armonk, NY (US)

(72) Inventors: Boaz Carmeli, Koranit (IL); Bilal Erhan, Brooklyn, NY (US); Takahiko Koyama, Scarsdale, NY (US); Kahn Rhrissorrakrai, Woodside, NY (US); Ajay Royyuru, Yorktown Heights, NY (US); Filippo Utro, White Plains, NY (US); Zeev Waks, Petach Tikva (IL)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 575 days.

(21) Appl. No.: 14/745,616

(22) Filed: Jun. 22, 2015

(65) Prior Publication Data

US 2016/0283608 A1  Sep. 29, 2016

Related U.S. Application Data

(63) Continuation of application No. 14/665,024, filed on Mar. 23, 2015.

(51) Int. Cl.
*G06F 16/901* (2019.01)
*G06F 16/2457* (2019.01)
*G16B 5/00* (2019.01)
*G16B 45/00* (2019.01)

(52) U.S. Cl.
CPC .... *G06F 16/9024* (2019.01); *G06F 16/24578* (2019.01); *G16B 5/00* (2019.02); *G16B 45/00* (2019.02)

(58) Field of Classification Search
None
See application file for complete search history.

(56) References Cited

U.S. PATENT DOCUMENTS

| | | | |
|---|---|---|---|
| 6,132,969 A | 10/2000 | Stoughton et al. | |
| 6,594,587 B2 | 7/2003 | Askenazi | |
| 7,657,379 B2 | 2/2010 | Stoughton et al. | |
| 7,974,788 B2 | 7/2011 | Rzhetsky et al. | |
| 8,068,994 B2 | 11/2011 | Draghici | |
| 8,489,334 B2 | 7/2013 | Chen et al. | |
| 2001/0034023 A1 | 10/2001 | Stanton et al. | |
| 2002/0123847 A1 | 9/2002 | Askenazi | |
| 2004/0249620 A1 | 12/2004 | Chandra et al. | |
| 2006/0020440 A1 | 1/2006 | Hellerstein | |
| 2009/0182513 A1 | 7/2009 | Draghici | |
| 2010/0057368 A1 | 3/2010 | Afeyan et al. | |
| 2012/0041683 A1 | 2/2012 | Vaske et al. | |
| 2012/0209625 A1 | 8/2012 | Armstrong | |
| 2012/0296090 A1 | 11/2012 | Wong | |
| 2013/0060543 A1 | 3/2013 | Di Bernardo et al. | |
| 2013/0096944 A1 | 4/2013 | Shah | |
| 2013/0144887 A1 | 6/2013 | Chen | |
| 2014/0193517 A1 | 7/2014 | Agarwal et al. | |

FOREIGN PATENT DOCUMENTS

| | | |
|---|---|---|
| WO | 0211048 A2 | 2/2002 |
| WO | 2014193982 A1 | 12/2014 |

OTHER PUBLICATIONS

Lex, "Entourage: Visualizing Relationships between Biological Pathways using Contextual Subsets," IEEE Transactions on Visualization and Computer Graphics, vol. 19(12), p. 2536-2545, 2013.*
List of IBM Patents or Patent Applications Treated As Related—Date Filed: Jul. 27, 2015; 2 page.
Boaz Carmeli, "Relevancy Assessment and Visualization of Biological Pathways" U.S. Appl. No. 14/665,024, filed Mar. 23, 2015.
List of IBM Patents or Patent Applications Treated As Related—Date Filed: Jun. 22, 2015; 2 pages.
Takahiko Koyama, et al. "Quantitative Assessment of Drug Recommendations" U.S. Appl. No. 14/968,140, filed Dec. 14, 2015.
Aittokallio, T. & Schwikowski, B. Graph-based methods for analysing networks in cell biology. Briefings in Bioinformatics 7, 243-255 (2006).
Andronis et al.; "Literature mining, ontologies and information visualization for drug repurposing"; Briefings in Bioinformatics, vol. 12, No. 4; Jun. 2011, pp. 357-368.
Chang, J. T. & Altman, "R.B. Extracting and Characterizing gene-drug relationships from the literature." Pharmacogenetics 14, 577-586 (2004).
Dijkstra et al.—"A note on two problems in connexion with graphs," Numerische Mathematik, vol. 1, No. 1, 1959, pp. 269-271.
Garten, Y. & Altman, R. "Pharmspresso: a text mining tool for extraction of pharmacogenomic concepts and relationships from full text." BMC Bioformatics 10, S6 (2009).
Lekka et al.; Literature analysis for systematic drug repurposing: a case study from Biovista; Drug Discovery Today: Therapeutic Strategies, vol. 8, No. 3-4; 2011, pp. 103-108.

(Continued)

*Primary Examiner* — G Steven Vanni
(74) *Attorney, Agent, or Firm* — Cantor Colburn LLP; Vazken Alexanian

(57) ABSTRACT

Embodiments are directed to computer implemented method of assessing a relevancy of a pathway to a disease of interest, the pathway having a source and a target. The method includes developing an impact of the source on the pathway. The method further includes developing a value of targeting, based at least in part on an alteration of the pathway, the pathway with a drug of interest. The method further includes identifying a relationship between the source and the target within the pathway. The method further includes combining: the impact of the source on the pathway; the value of targeting, based at least in part on the alteration of the pathway, the pathway with a drug of interest; and the relationship between the source and the target within the pathway, wherein the combining results in an assessment that represents the relevancy of the pathway to the disease of interest.

5 Claims, 10 Drawing Sheets

(56) References Cited

OTHER PUBLICATIONS

Nhgri, National Human Genome Research Institute, "Biological Pathways Fact Sheet," www.genome.gov/27530687, revised Jun. 12, 2012, downloaded May 16, 2016.

Nikolsky, Y., Nikolskaya, T. & Bugrim, A. Biological networks and analysis of experimental data in drug discovery. Drug Discovery Today 10, 653-662 (2005).

Partl et al., "enroute: Dynamic path extraction from biological pathway maps for in-depth experimental data analysis," IEEE Symposium on Biological Data Visualization (BioVis), 2012, pp. 107-114.

Viswanathan et al., "Getting started in biological pathway construction and analysis," PLoS Computational Biology, vol. 4, No. 2, 2008, e16, 5 pages.

Gang, "Biological network analysis and its application in complex disease research," 2012, Central South University, PhD dissertation, pp. 1-69. English abstract. doi: 10.76661d.y2198637.

\* cited by examiner $$A = \frac{\sum a_i \partial_i}{\sum a_i}$$

$$B = \frac{\sum b_i \partial_i}{\sum b_i}$$

$$\text{ALTERNATIVE } B = \frac{\sum b_i \partial_i}{M \sum b_i}$$

$$C = \frac{\sum c_{ij} \partial_{ij}}{\sum c_{ij}}$$

$$\text{RELEVANCE SCORE} = \frac{A + B + C}{3}$$

FIG. 3B

| PATHWAY NAME | VALUE/ RELEVANCE | NUMBER OF MUTATION(S) IN THE PATHWAYS | NUMBER OF DRUGGABLE GENE(S) IN THE PATHWAYS |
|---|---|---|---|
| DIRECT p53 EFFECTORS | 0.64303 | 4 | 20 |
| NECTIN ADHESION PATHWAY | 0.581744 | 5 | 92 |
| p53 PATHWAY | 0.581062 | 4 | 21 |
| S1P1 PATHWAY | 0.578269 | 5 | 92 |
| PDGFR-BETA SIGNALING PATHWAY | 0.57537 | 5 | 92 |
| SPHINGOSINE 1-PHOSPHATE (S1P) PATHWAY | 0.573756 | 5 | 97 |
| UROKINASE-TYPE PLASMINOGEN ACTIVATOR (uPA) AND uPAR-MEDIATED SIGNALING | 0.573026 | 5 | 93 |
| ErbB1 DOWNSTREAM SIGNALING | 0.57214 | 5 | 89 |
| ErbB RECEPTOR SIGNALING NETWORK | 0.571322 | 5 | 90 |
| EGF RECEPTOR (ErbB1) SIGNALING PATHWAY | 0.570642 | 5 | 89 |
| INTERNALIZATION OF ErbB1 | 0.570642 | 5 | 89 |
| PROTEOGLYCAN SYNDECAN-MEDIATED SIGNALING EVENTS | 0.568065 | 5 | 70 |
| GLYPICAN PATHWAY | 0.502387 | 4 | 73 |
| SIGNALING EVENTS MEDIATED BY FOCAL ADHESION KINASE | 0.494343 | 4 | 61 |
| PAR1-MEDIATED THROMBIN SIGNALING EVENTS | 0.492732 | 4 | 59 |
| Thrombin_protease-activated receptor (PAR) PATHWAY | 0.492732 | 4 | 59 |
| CLASS I PI3K SIGNALING EVENTS | 0.487257 | 4 | 56 |
| SIGNALING EVENTS MEDIATED BY HEPATOCYTE GROWTH FACTOR RECEPTOR (C-MET) | 0.486789 | 4 | 62 |
| SYNDECAN-1-MEDIATED SIGNALING EVENTS | 0.485637 | 4 | 62 |
| IL5-MEDIATED SIGNALING EVENTS | 0.484598 | 4 | 56 |
| IL3-MEDIATED SIGNALING EVENTS | 0.483646 | 4 | 56 |
| GMCSF-MEDIATED SIGNALING EVENTS | 0.483333 | 4 | 56 |
| GLYPICAN 1 NETWORK | 0.482243 | 4 | 66 |
| TRAIL SIGNALING PATHWAY | 0.472639 | 4 | 59 |
| CLASS I PI3K SIGNALING EVENTS MEDIATED BY Akt | 0.424603 | 4 | 42 |
| AP-1 TRANSCRIPTION FACTOR NETWORK | 0.371001 | 4 | 17 |
| CDC42 SIGNALING EVENTS | 0.368685 | 4 | 17 |
| REGULATION OF CDC42 ACTIVITY | 0.360749 | 4 | 14 |
| LKB1 SIGNALING EVENTS | 0.324759 | 3 | 19 |
| IFN-GAMMA PATHWAY | 0.309212 | 3 | 22 |

FIG. 5

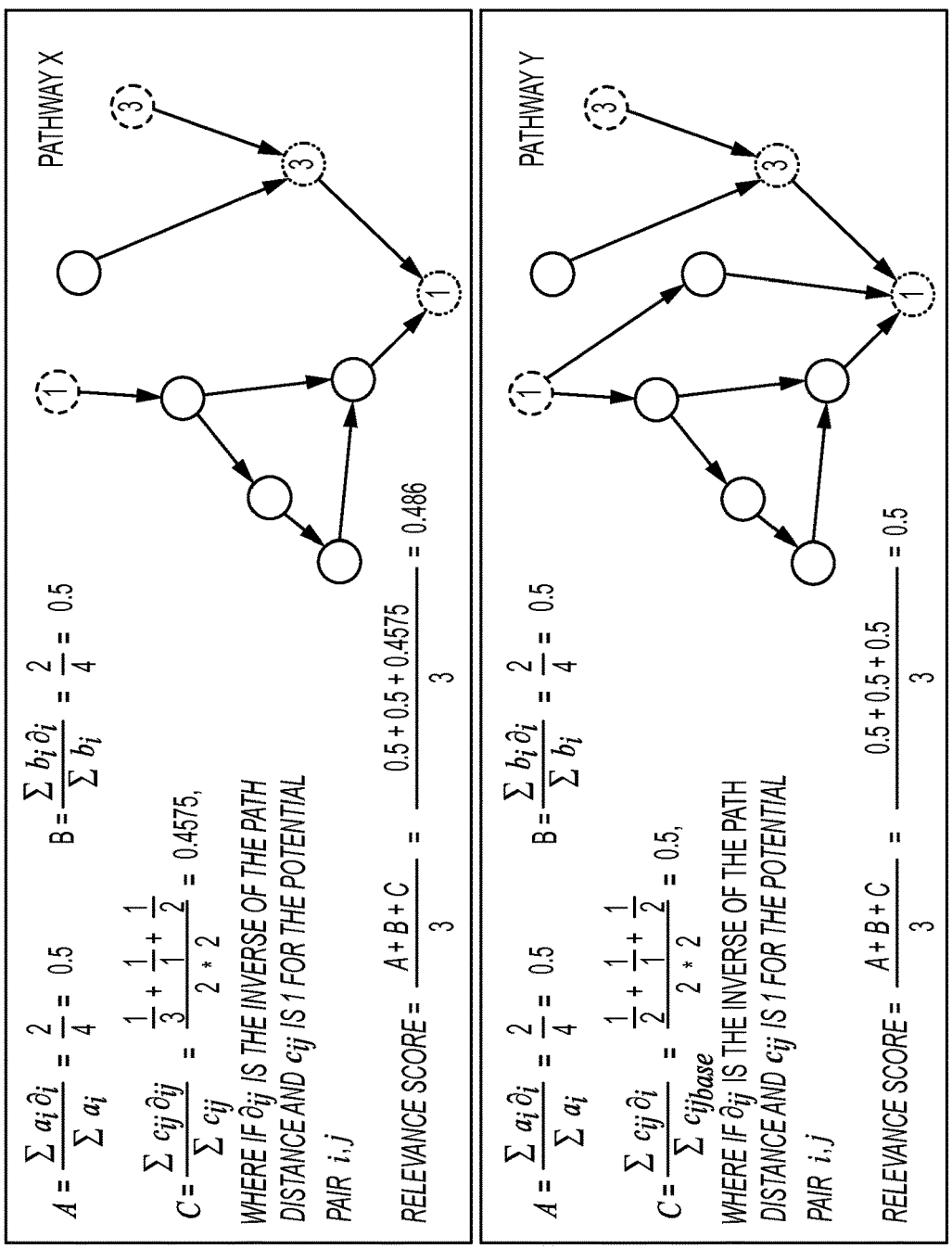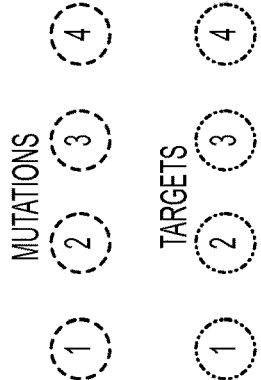
FIG. 6

SIMPLIFIED VISUALIZATION AND RELEVANCY ASSESSMENT OF BIOLOGICAL PATHWAYS

DOMESTIC PRIORITY

The present application claims priority to U.S. Nonprovisional application Ser. No. 14/665,024 filed on Mar. 23, 2015 titled "RELEVANCY ASSESSMENT AND VISUALIZATION OF BIOLOGICAL PATHWAYS," assigned to the assignee hereof and expressly incorporated by reference herein.

BACKGROUND

The present disclosure relates in general to assessing and visualizing biological pathways. More specifically, the present disclosure relates to systems and methodologies for assessing a relevance of a biological pathway to a particular disease state, and for simplifying visualization of the biological pathway that was assessed as relevant to the particular disease state.

Numerous genome-wide association studies of diseases have suggested thousands of causal and correlative links between DNA sequence variants and specific disease phenotypes. These suspected or validated variants often reside within genes and open reading frames that can be mapped to biological pathways. A biological pathway is an ordered set of interactions between intracellular molecules having collective activity that impacts cellular function, for example, by controlling metabolite synthesis or by regulating the expression of sets of genes.

A diagram depicting exemplary biological pathways of a typical cell is shown in FIG. 1. As shown, cells are constantly receiving cues from both inside and outside the body, which are prompted by stimuli such as injury, infection, stress or even food. To react and adjust to these cues, cells send and receive signals through biological pathways. Some of the most common biological pathways are involved in metabolism, the regulation of genes and the transmission of signals. The majority of cellular pathways can be classified as signaling pathways (impacting gene expression) or metabolic pathways (regulating biochemical synthesis). While some molecules, like oxygen, can easily travel through the cell membrane, signals go through structures on the cell surface, called receptors. After interacting with a receptor, the signal travels through the cell where its message is transmitted and changed by specialized proteins or other molecules residing in the cell. Signals can be involved in chemical reactions, triggering the assembly of new molecules, inducing cell movement, turning genes on or off, or even changing the shape of a cell. A given gene can reside in multiple pathways and can alter the activity of multiple downstream pathways. Therefore, a function-altering variant within a single gene can impact more than one pathway. Pathways play a key role in the advancement of our understanding of biological processes in the cell.

Pathway information is available through a large number of databases ranging from high quality databases created by professional curators to massive databases covering a vast number of pathways created through natural language processing (NLP) and text mining of abstracts. For example, some pathway databases provide detailed metabolic pathways, while other pathway databases provide detailed signaling pathways. Because of the differences in size, quality and or property, it can be a challenge to select a pathway database, and further to identify the pathways with the selected pathway database, that are aligned with the user's purpose.

A typical pathway database includes the capability to visualize pathways through pathway diagrams, which combine metabolic, genetic and signaling networks based on the literature. Software applications are available that allow for the production, editing and analysis of pathway diagrams. A pathway diagram is usually represented via a directed graph. A directed graph (or digraph, or directed network) is a graph or a set of objects called vertices or nodes that are connected together, wherein all the edges are directed from one vertex to another. The ability to visualize pathway diagrams plays a fundamental role in interpreting and understanding biological processes.

SUMMARY

Embodiments are directed to a computer implemented method of assessing a relevancy of at least one pathway to a disease of interest, the at least one pathway having a source and a target. The method includes developing, by a processor, an impact of the source on the at least one pathway. The method further includes developing, by the processor, a value of targeting, based at least in part on an alteration of the at least one pathway, the at least one pathway with a drug of interest. The method further includes identifying, by the processor, a relationship between the source and the target within the at least one pathway. The method further includes combining: the impact of the source on the at least one pathway; the value of targeting, based at least in part on the alteration of the at least one pathway, the at least one pathway with the drug of interest; and the relationship between the source and the target within the at least one pathway, wherein the combining results in an assessment that represents the relevancy of the at least one pathway to the disease of interest.

Embodiments are further directed to a computer system for assessing a relevancy of at least one pathway to a disease of interest, the at least one pathway having a source and a target. The system includes a processor configured to develop an impact of the source on the at least one pathway. The system further includes the processor configured to develop a value of targeting, based at least in part on an alteration of the at least one pathway, the at least one pathway with at least one drug. The system further includes the processor configured to identify a relationship between the source and the target within the at least one pathway. The system further includes the processor configured to combine: the impact of the source on the at least one pathway; the value of targeting, based at least in part on the alteration of the at least one pathway, the at least one pathway with the drug of interest; and the relationship between the source and the target within the at least one pathway, wherein the combining by the processor results in an assessment that represents the relevancy of the at least one pathway to the disease of interest.

Embodiments are further directed to a computer program product for assessing a relevancy of at least one pathway to a disease of interest, the at least one pathway having a source and a target. The computer program product includes a computer readable storage medium having program instructions embodied therewith, wherein the computer readable storage medium is not a transitory signal per se, and the program instructions are readable by a processor circuit to cause the processor circuit to perform a method. The method includes developing an impact of the source on the at least one pathway. The method further includes developing a value of targeting, based at least in part on an alteration of the at least one pathway, the at least one pathway with a drug of interest. The method further includes identifying a relationship between the source and the target within the at least one pathway. The method further includes combining: the impact of the source on the at least one pathway; the value of targeting, based at least in part on the alteration of the at least one pathway, the at least one pathway with the drug of interest; and the relationship between the source and the target within the at least one pathway, wherein the combining results in an assessment that represents a relevancy of the at least one pathway to the disease of interest.

Embodiments are further directed to a computer implemented method of simplifying a visualization of at least one pathway. The method includes creating a graph of the at least one pathway, wherein the graph comprises a plurality of nodes connected by edges. The method further includes identifying relevant paths of the graph. The method further includes removing from the relevant paths non-informative or non-significant nodes to create a first subgraph. The method further includes simplifying relations and relative attributes of the first subgraph to create a second, simplified subgraph.

Embodiments are further directed to a computer system for simplifying a visualization of at least one pathway. The system includes a processor configured to create a graph of the at least one pathway, wherein the graph comprises a plurality of nodes connected by edges. The system further includes the processor configured to identify relevant paths of the graph. The system further includes the processor configured to remove from the relevant paths non-informative or non-significant nodes to create a first subgraph. The system further includes the processor further configured to simplify relations and relative attributes of the first subgraph to create a second, simplified subgraph.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present disclosure is particularly pointed out and distinctly claimed in the claims at the conclusion of the specification. The foregoing and other features and advantages are apparent from the following detailed description taken in conjunction with the accompanying drawings in which:

FIG. 3B depicts equations that may be implemented by modules of the system shown in FIG. 3A in accordance with one or more embodiments;

FIG. 5 depicts a table illustrating exemplary pathway assessment results in accordance with one or more embodiments;

FIG. 6 depicts diagrams illustrating examples of how pathway assessments of the system shown in FIG. 3A may be implemented in accordance with one or more embodiments;

Figure 1:
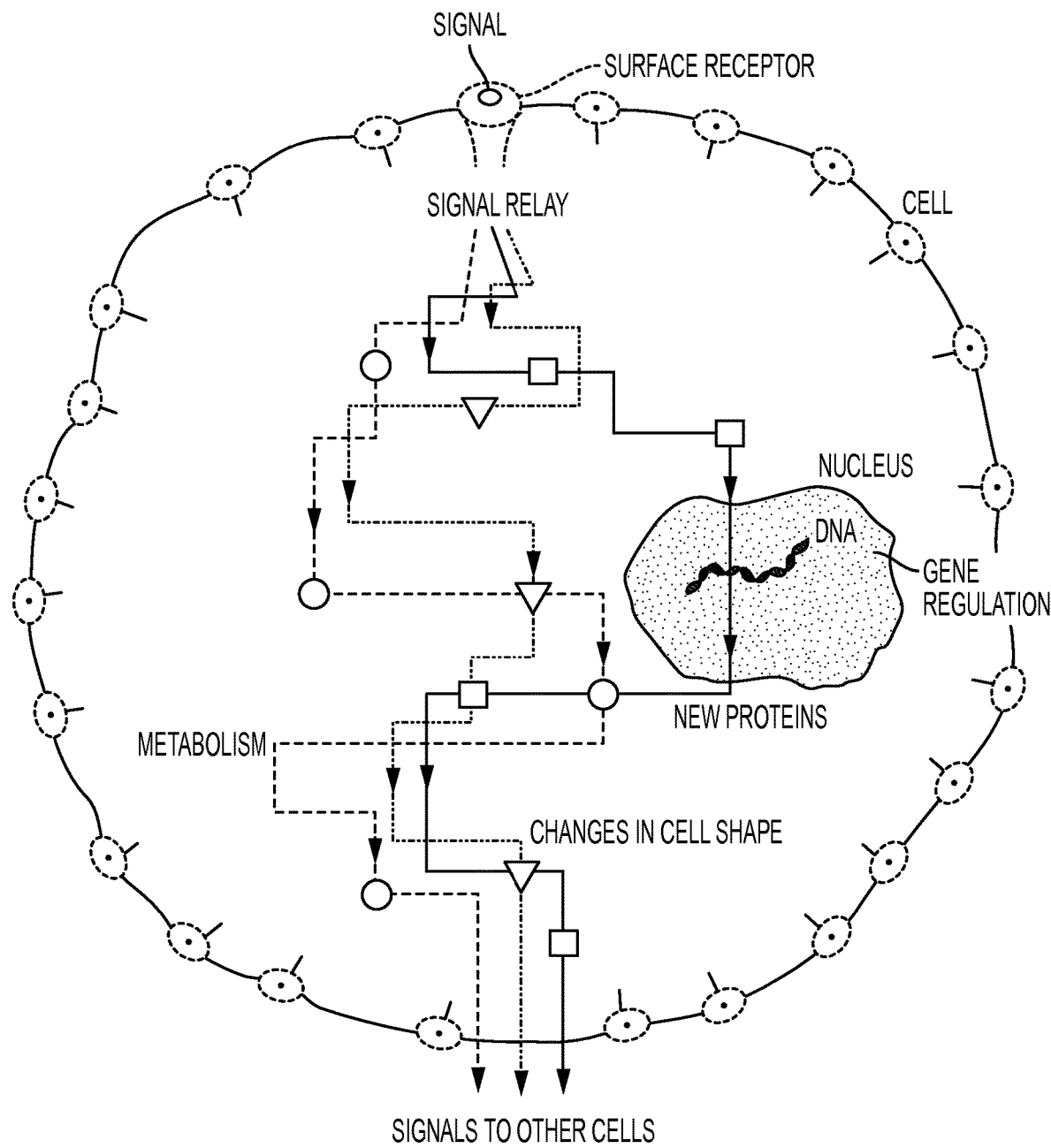
FIG. 1 is a diagram depicting exemplary biological pathways of a typical cell.

In the accompanying figures and following detailed description of the disclosed embodiments, the various elements illustrated in the figures are provided with three or four digit reference numbers. The leftmost digit(s) of each reference number corresponds to the figure in which its element is first illustrated.

DETAILED DESCRIPTION

Various embodiments of the present disclosure will now be described with reference to the related drawings. Alternate embodiments may be devised without departing from the scope of this disclosure. It is noted that various connections are set forth between elements in the following description and in the drawings. These connections, unless specified otherwise, may be direct or indirect, and the present disclosure is not intended to be limiting in this respect. Accordingly, a coupling of entities may refer to either a direct or an indirect connection.

A biological pathway is a series of actions among molecules in a cell that leads to a certain product or a change in a cell. Exemplary cell pathways for metabolism, effecting changes in cell shape and creating new proteins are shown in FIG. 1. Such pathways can trigger the assembly of new molecules, such as a fat or a protein. Pathways can also turn genes on and off, or spur a cell to move. Thus, pathways constantly transport signals or cues to cells from both inside and outside the body, which are prompted by such things as injury, infection, stress or even food. To react and adjust to these cues, cells also send signals and cues through biological pathways. The molecules that make up biological pathways interact with signals, as well as with each other, to carry out their designated tasks. Biological pathways can act over short or long distances. For example, some cells send out signals to nearby cells to repair localized damage, such as a scratch on your knee. Other cells produce substances, such as hormones, that travel through your blood to distant target cells. Biological pathways can also produce small or large outcomes. For example, some pathways subtly affect how the body processes drugs, while others play a major role in how a fertilized egg develops into a baby.

There are many types of biological pathways. Some of the most common are involved in metabolism, the regulation of genes and the transmission of signals. Metabolic pathways make possible the chemical reactions that occur in our bodies. An example of a metabolic pathway is the process by which human cells break down food into energy molecules that can be stored for later use. Other metabolic pathways actually help to build molecules. Gene regulation pathways turn genes on and off. Such action is vital because genes produce proteins, which are the key component needed to carry out nearly every task in our bodies. Proteins make up our muscles and organs, and help our bodies move and defend us against germs. Signal transduction pathways move a signal from a cell's exterior to its interior. Different cells are able to receive specific signals through structures on their surface, called receptors. After interacting with a receptor, the signal travels through the cell where its message is transmitted by specialized proteins that trigger a specific action in the cell. For example, a chemical signal from outside the cell might be turned into a protein signal inside the cell. In turn, that protein signal may be converted into a signal that prompts the cell to move.

Biological pathways do not always work properly. When something goes wrong in a pathway, the result can be a disease such as cancer or diabetes. Researchers often learn about human disease from studying biological pathways. Identifying what genes, proteins and other molecules are involved in a biological pathway can provide clues about what goes wrong when a disease strikes. For example, researchers may compare certain biological pathways in a healthy person to the same pathways in a person with a disease to assist in discovering the roots of the disorder.

The identification of relevant pathways from a set of genes is often the first step in implementing this research philosophy. However, determining the pathways that are most relevant for a set of diseased genes is challenging, and is often made even more difficult by differences in pathway composition and topology that are present between different pathway repositories. For example, problems in any number of steps along a biological pathway can often lead to the same disease. Genetic mutations also complicate the identification of relevant pathways for disease state. For example, cancer is a genomic disease associated with a plethora of gene mutations. Among these mutated genes, driver genes are defined as being causally linked to the formation and development of tumors, while passenger genes are thought to be irrelevant for cancer development. Different genetic mutations can lead to the same cancer in different patients. Instead of attempting to discover ways to attack one well-defined genetic enemy, this complex view can be simplified by identifying and focusing on the biological pathways that are disrupted by the genetic mutations. Rather than designing dozens of drugs to target dozens of mutations, drug developers could focus their attentions on just two or three biological pathways. Patients could then receive the one or two drugs most likely to work for them based on the pathways affected in their particular tumors.

The accurate identification of pathways that are involved in a disease, and of the steps of the identified pathways that are affected in each patient, may lead to more personalized strategies for diagnosing, treating and preventing disease. Researchers currently are using information about biological pathways to develop new and better drugs. Additionally, pathway information may also be used to more effectively choose and combine existing drugs. With increasing numbers of large scale genomic datasets available, integrating these genomic data to identify driver genes from aberration regions of cancer genomes becomes an important goal of cancer genome analysis and investigations into mechanisms responsible for cancer development.

The present disclosure provides systems and methodologies to assess the value of targeting a biological pathway for its relevance to a disease of interest, wherein biological pathways having the highest relevance may be more easily identified. The present disclosure further provides systems and methodologies to take a pathway that has been identified as of high relevance and improve the ability to visualize the high relevance pathway. In one or more embodiments, the disclosed systems and methodologies make an assessment of sources (e.g., mutated genes) and targets (e.g., druggable molecular entities) that can be targeted downstream of the source, thereby identifying the biological pathways that merit investigation. In one or more embodiments, the disclosed systems and methodologies further provide a simplified visualization of the identified biological pathways that merit investigation. Accordingly, the operation of a computer system implementing one or more of the disclosed embodiments can be improved.

Figure 2:
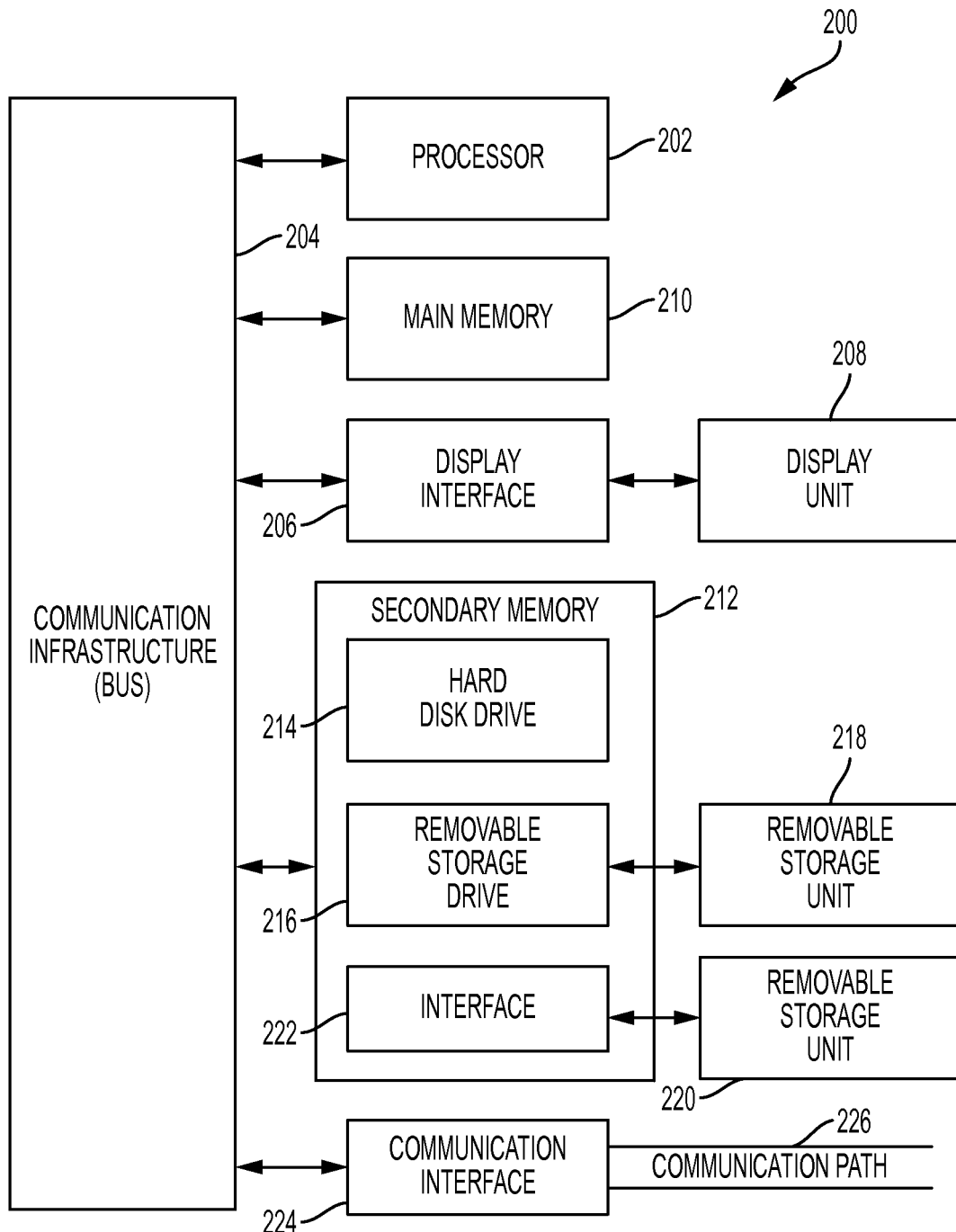
FIG. 2 depicts an exemplary computer system capable of implementing one or more embodiments of the present disclosure.

Turning now to the drawings in greater detail, wherein like reference numerals indicate like elements, FIG. 2 illustrates a high level block diagram showing an example of a computer-based information processing system 200 useful for implementing one or more embodiments of the present disclosure. Although one exemplary computer system 200 is shown, computer system 200 includes a communication path 226, which connects computer system 200 to additional systems (not depicted) and may include one or more wide area networks (WANs) and/or local area networks (LANs) such as the Internet, intranet(s), and/or wireless communication network(s). Computer system 200 and additional system are in communication via communication path 226, e.g., to communicate data between them.

Computer system 200 includes one or more processors, such as processor 202. Processor 202 is connected to a communication infrastructure 204 (e.g., a communications bus, cross-over bar, or network). Computer system 200 can include a display interface 206 that forwards graphics, text, and other data from communication infrastructure 204 (or from a frame buffer not shown) for display on a display unit 208. Computer system 200 also includes a main memory 210, preferably random access memory (RAM), and may also include a secondary memory 212. Secondary memory 212 may include, for example, a hard disk drive 214 and/or a removable storage drive 216, representing, for example, a floppy disk drive, a magnetic tape drive, or an optical disk drive. Removable storage drive 216 reads from and/or writes to a removable storage unit 218 in a manner well known to those having ordinary skill in the art. Removable storage unit 218 represents, for example, a floppy disk, a compact disc, a magnetic tape, or an optical disk, etc. which is read by and written to by removable storage drive 216. As will be appreciated, removable storage unit 218 includes a computer readable medium having stored therein computer software and/or data.

In alternative embodiments, secondary memory 212 may include other similar means for allowing computer programs or other instructions to be loaded into the computer system. Such means may include, for example, a removable storage unit 220 and an interface 222. Examples of such means may include a program package and package interface (such as that found in video game devices), a removable memory chip (such as an EPROM, or PROM) and associated socket, and other removable storage units 220 and interfaces 222 which allow software and data to be transferred from the removable storage unit 220 to computer system 200.

Computer system 200 may also include a communications interface 224. Communications interface 224 allows software and data to be transferred between the computer system and external devices. Examples of communications interface 224 may include a modem, a network interface (such as an Ethernet card), a communications port, or a PCM-CIA slot and card, etcetera. Software and data transferred via communications interface 224 are in the form of signals which may be, for example, electronic, electromagnetic, optical, or other signals capable of being received by communications interface 224. These signals are provided to communications interface 224 via communication path (i.e., channel) 226. Communication path 226 carries signals and may be implemented using wire or cable, fiber optics, a phone line, a cellular phone link, an RF link, and/or other communications channels.

In the present disclosure, the terms "computer program medium," "computer usable medium," and "computer readable medium" are used to generally refer to media such as main memory 210 and secondary memory 212, removable storage drive 216, and a hard disk installed in hard disk drive 214. Computer programs (also called computer control logic) are stored in main memory 210 and/or secondary memory 212. Computer programs may also be received via communications interface 224. Such computer programs, when run, enable the computer system to perform the features of the present disclosure as discussed herein. In particular, the computer programs, when run, enable processor 202 to perform the features of the computer system. Accordingly, such computer programs represent controllers of the computer system.

Figure 3A:
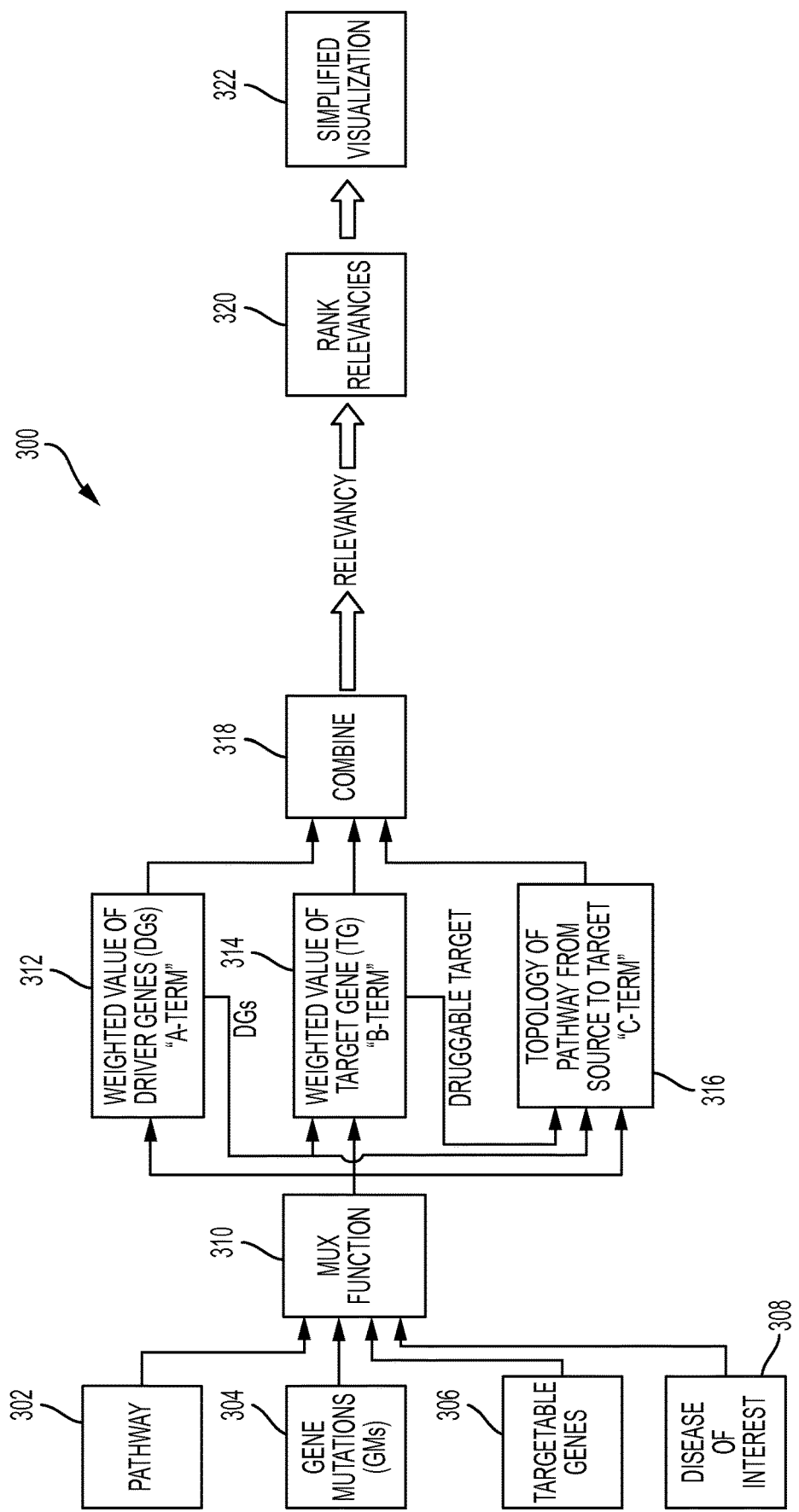
FIG. 3A depicts a diagram of an exemplary system in accordance with one or more embodiments.

FIG. 3A depicts a diagram of an assessment and visualization system 300 in accordance with one or more embodiments. The various functional modules of assessment and visualization system 300 may be implemented using computer-based information processing system 200 shown in FIG. 2. As shown in FIG. 3A, assessment and visualization system 300 includes pathway inputs 302, gene mutations (GMs) inputs 304, targetable genes inputs 306, disease of interest inputs 308, a multiplex (MUX) module 310, a weighted value of driver genes (DGs) module 312, a weighted value of target gene (TG) module 314, a topology of the pathway from source to target module 316, a combine module 318, a rank relevancies module 320 and a simplified visualization module 322, configured and arranged as shown.

In its overall operation, assessment and visualization system 300 ranks the pathways contained in a chosen pathway database based on a quantitative determination of the likelihood that a given pathway in the database is involved in the development of, or relevant to the treatment of, a selected disease. The determination that a given pathway in the database is involved in the development of or relevant to the treatment of, a selected disease is based at least in part on the identification of genes in the pathway that advance the pathway toward the selected disease state.

A GM is a change in DNA sequence that makes up a gene. GMs complicate the identification of relevant pathways for disease state. For example, cancer is a genomic disease associated with a plethora of GMs. Among these GMs, DGs are defined as the GMs that are causally linked to the formation and development of tumors, while passenger genes are GMs thought to be irrelevant for cancer development. Different DGs can lead to the same cancer in different patients. In general, for purposes of the present disclosure, the term DG is used to refer to a GM that advances (or drives) a pathway that is involved in some kind of disease. There are many DGs that drive many pathways that can result in a given disease. For a given disease, there are typically a certain number of DGs (e.g., 15 to 20) that are most significant.

As shown in FIG. 3A, the initial data inputs to system 300 are a selected pathway database (pathway inputs 302), a selected pool of GMs for a given disease of interest (GMs inputs 304), the druggable (TGs)s associated with the disease of interest (targetable genes inputs 306) and a disease of interest (disease of interest inputs 308). The pathway database may be selected based on a number of factors. In the present disclosure, one or more embodiments consider a cancer-specific, hand curated pathway database known as NCI-PID. Other considerations in selecting a suitable pathway database include but are not limited to: the level of curation (e.g., manual vs. NLP); cancer and/or other disease-specific biological pathways; the degree of experimental support for the pathway; high throughput vs. low throughput data sources; the desire for human, mammalian other animal and plant data sources; orthology based links; and the type of interactions desired (e.g., physical, logical, correlative, etc.).

A disease of interest is selected based on the needs and interests of the individual user. Once a disease of interest (disease of interest input 308) is identified, the most significant genes and gene mutations (GMs inputs 304) involved in the selected disease can then be identified. In general, GMs inputs 304 may be compiled from existing literature or databases. Additionally, known computational and informatics methods for inferring the most significant GMs may also be utilized. The method for determining the pool of GMs is dependent on the application, e.g. a clinical treatment or a basic research application.

Once a disease of interest (disease of interest input 308) is identified, the druggable target genes (targetable genes 306) associated with the disease of interest can also be identified. For example, druggable target genes may be compiled from existing literature or databases. Computational and informatics methods may also be used to infer druggable targets. The particular method chosen for determining a pool of druggable target genes is dependent on the application, e.g. a clinical treatment or a basic research application.

MUX module 310 receives inputs from pathway inputs 302, GMs inputs 304, targetable genes inputs 306 and disease of interest inputs 308, and selectively provides them to modules 312, 314 and 316 according to a general multiplex functionality. Module 312 calculates a weighted value of the DGs. In one or more embodiments, module 312 calculates the weighted value of the DGs according to an A-term, shown in FIG. 3B. In the A-term, a, is a number that weights the presence of each of the "i" GMs. Thus, "a" can take into account cnv (copy number variations), number of DGs, etcetera. Thus, "a" identifies the GMs that are more meaningful than others. The value of "a" can be derived from external knowledge, for example the level of activity of the GM and its presumed importance in the pathway of interest. There is considerable flexibility on the selection of "a". For example, "a" could be implemented as a Bayesian model, support vector machine, and the like. The flexibility in the selection of "a" allows it to be changed over time as the input data to system 300 improves and changes over time.

Continuing with the A-term shown in FIG. 3B, $\partial_i$ is a binary term that is zero (0) if the GM does not reside in the current pathway of interest, and is a one (1) if the GM resides in the current pathway of interest. In other words, $\partial_i$ is a one (1) if the GM is a DG for the current pathway of interest, and $\partial_i$ is a zero (0) if the GM is not a DG for the pathway of interest. It is noted that at this stage of the process, the A-term and subsequent relevancy (i.e., output of module 318) are determined for a specific pathway in isolation of any other pathway, but will be subsequently used to compare the relevancies between pathways. Thus, the binary term $\partial_i$ has the effect of eliminating from the numerator of the A-term any GM that is not in a current pathway of interest that leads to a particular disease of interest. It is noted that system 300 and its associated methodologies evaluate a set of GMs that are initially thought to be relevant for a given patient in the context of the particular disease of interest. Accordingly, all of the GMs are evaluated against a set of predefined pathways. Thus, there will be some pathways that do not contain any of the patient-specific GMs. The source of $\partial_i$ is a simple search of the current pathway of interest. Thus, whether the GM is present or not will determine whether $\partial_i$ is a one (1) or a zero (0), respectively.

Accordingly, the A-term provides a representation of the relevancy of a current pathway of interest versus all other pathways considered. If the "a" values for all pathways of interest are equal, then the A-term will represent the sensitivity of that pathway to capturing the set of GMs. When the "a" values for all pathways of interest are not equally weighted, then the A-term will represent the relevancy with respect to the considerations that support the calculation of "a." In other words, the A-term represents the percentage of the initial GM pool that are DGs, and therefore most likely to advance a pathway that results in a particular disease of interest. The higher the A-term, the greater impact the identified DGs are expected to have on the pathway.

Module 314 calculates a weighted value of the TG. In one or more embodiments, module 314 calculates the weighted value of the TG according to a B-term, shown in FIG. 3B. The B-term is similar in structure to the A-term. While the A-term focuses on an identification and assessment of the DGs, the B-term focuses on an identification and assessment of the TG. Thus, the B-term also takes into account the DGs identified as part of the A-term calculation. In the B-term, for all drug targets from 1 to "i," $b_i$ is a number that weights the considerations associated with targeting the "i" druggable gene, for example the centrality of the gene in a signaling network. The value of $b_i$ can include items such as the nature and efficacy of the specific drug(s) targeting the gene or the level of activity of a gene "i." Continuing with the B-term, $\partial_i$ is a binary term that is zero (0) if the druggable gene "i" is not upstream and/or downstream of any mutated genes (e.g., DGs) in the current pathway of interest, and $\partial_i$ assumes the value one (1) if the druggable gene "i" is upstream and/or downstream of any mutated genes (e.g., DGs) in the current pathway of interest.

Alternatively, the B-term may also be given by an alternative B-term equation shown in FIG. 3B, wherein M is provided in the numerator as shown. M may be defined as the number of druggable gene targets across a set of pathways. M functions as a normalization term, which ensures that the alternative B-term is a real value between zero (0) and one (1). In the alternative B-term calculation, in addition to a weighting of targeting gene "i," the value of $b_i$ may also be modified to account for the potential effects of mutations present upstream and downstream of gene "i" on drugs targeting "i," for example by taking the ratio of mutations upstream of "i" to all mutations upstream and downstream of "i."

Accordingly, the B-term provides a representation of a relevancy of a current pathway of interest versus all other pathways considered. If the "b" values for all pathways of interest are equal, then the B-term merely represents the sensitivity of that pathway to capturing the set of druggable target genes. When the "b" values for all pathways of interest are not equally weighted, then the B-term represents the relevancy with respect to the considerations that support the calculation of "b."

Module 316 calculates a topology of the pathway from source to target. In one or more embodiments, module 316 calculates the topology of the pathway from source to target according to a C-term, shown in FIG. 3B. The C-term is similar in structure to the A-term and the B-term. While the A-term focused on an identification and assessment of the DGs, and the B-term focuses on an identification and assessment of the TGs, the C-term focuses on the relationship between the A-term and the B-term, and also takes into account both the DGs identified by the A-term and the druggable target identified by the B-term. In the C-term, for all DGs from 1 to "i," and for all druggable targets from one (1) to "j," $\partial_{ij}$ assumes the value one (1) if either the druggable gene "i" is downstream of the mutated gene "j" (i.e., DG) in the pathway or if "i" is a druggable gene and equal to "j." Otherwise, $\partial_{ij}$ assumes the value of zero (0). Continuing with the C-term, "d" is the number of druggable target(s) present in the current pathway of interest with pathways to a DG, and "n" is the number of DGs in the current pathway of interest. Finally in the C-term, $c_{ij}$ is a real number that weights the relationship between individual DG "i" and individual TG "j." For instance, the value of $c_{ij}$ can be based on the distance (i.e., number of protein/small molecule) and/or directionality between the individual DG "i" and the individual TG "j," or the value of $c_{ij}$ can be based on the frequency at which the individual DG "i" is in a path to any DG.

Figure 7A:
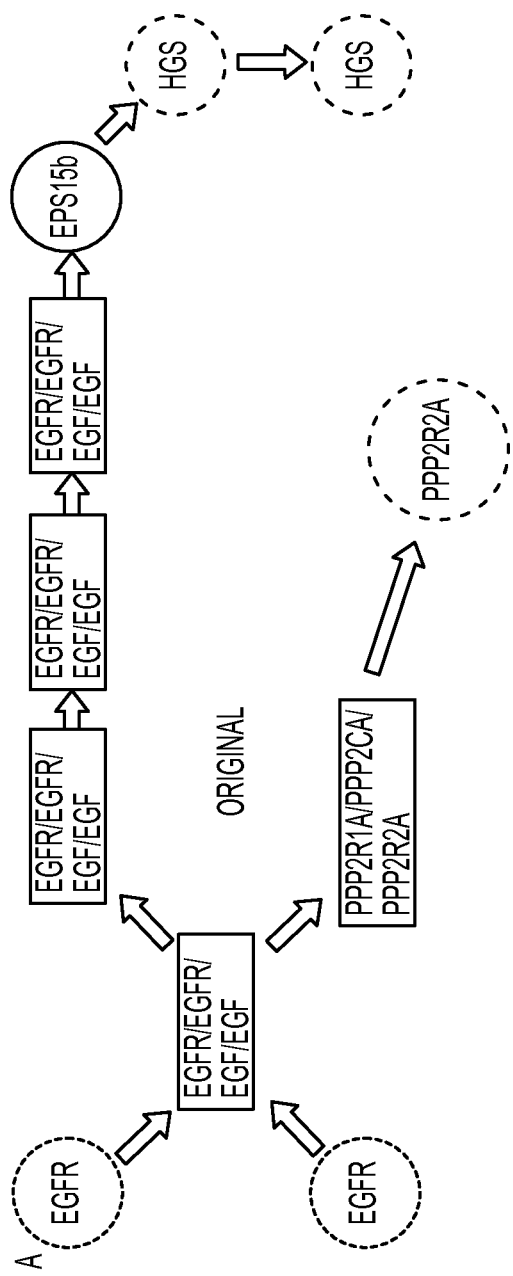
FIG. 7A depicts a graph illustrating portions of an un-simplified pathway.
Figure 7B:
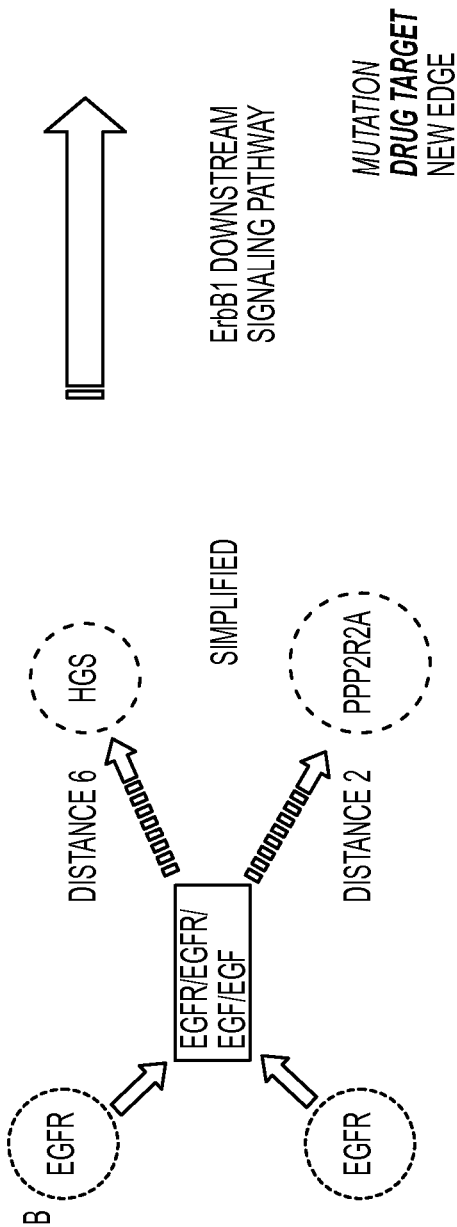
FIG. 7B depicts a graph illustrating portions of a simplified version of the pathway shown in FIG. 7A in accordance with one or more embodiments.
Figure 8:
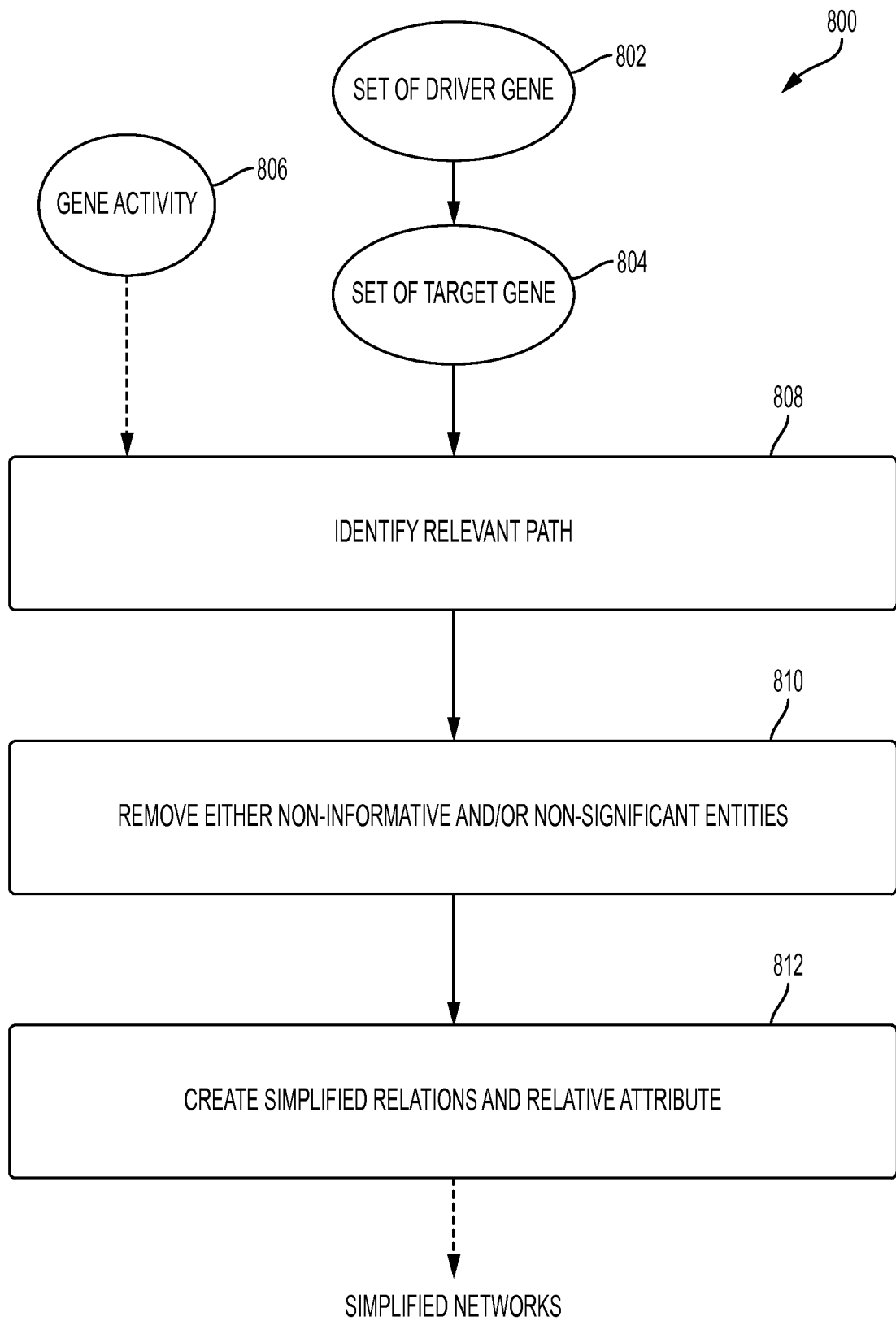
FIG. 8 depicts a flow diagram illustrating a methodology in accordance with one or more embodiments.

Module 318 combines the outputs of the assessments made by modules 312, 314 and 316 and determines a relevancy of the current pathway of interest. In one or more embodiments, the relevancy of the current pathway of interest may be implemented as a computed relevance score (shown in FIG. 3B) that represents the relevancy of the current pathway of interest. Module 320 assembles and ranks the relevancies serially computed by module 318, and module 322 simplifies the visualization of pathways ranked by module 320. The rankings identified by modules 318 and 320 allow simplified visualization module 322 to focus on pathways having the highest relevancies. In addition to the relevance score shown in FIG. 3B, the pathway relevancies may include other criteria of the ranked pathways, including but not limited to the number of mutations in the pathway or the number of druggable genes in the pathway. FIG. 5 depicts an exemplary table illustrating how the relevancy rankings identified by modules 318 and 320 may be organized and displayed. FIGS. 7A, 7B and 8 depict additional details of simplified visualization module 322 and will be described in more detail later in this disclosure.

Figure 4:
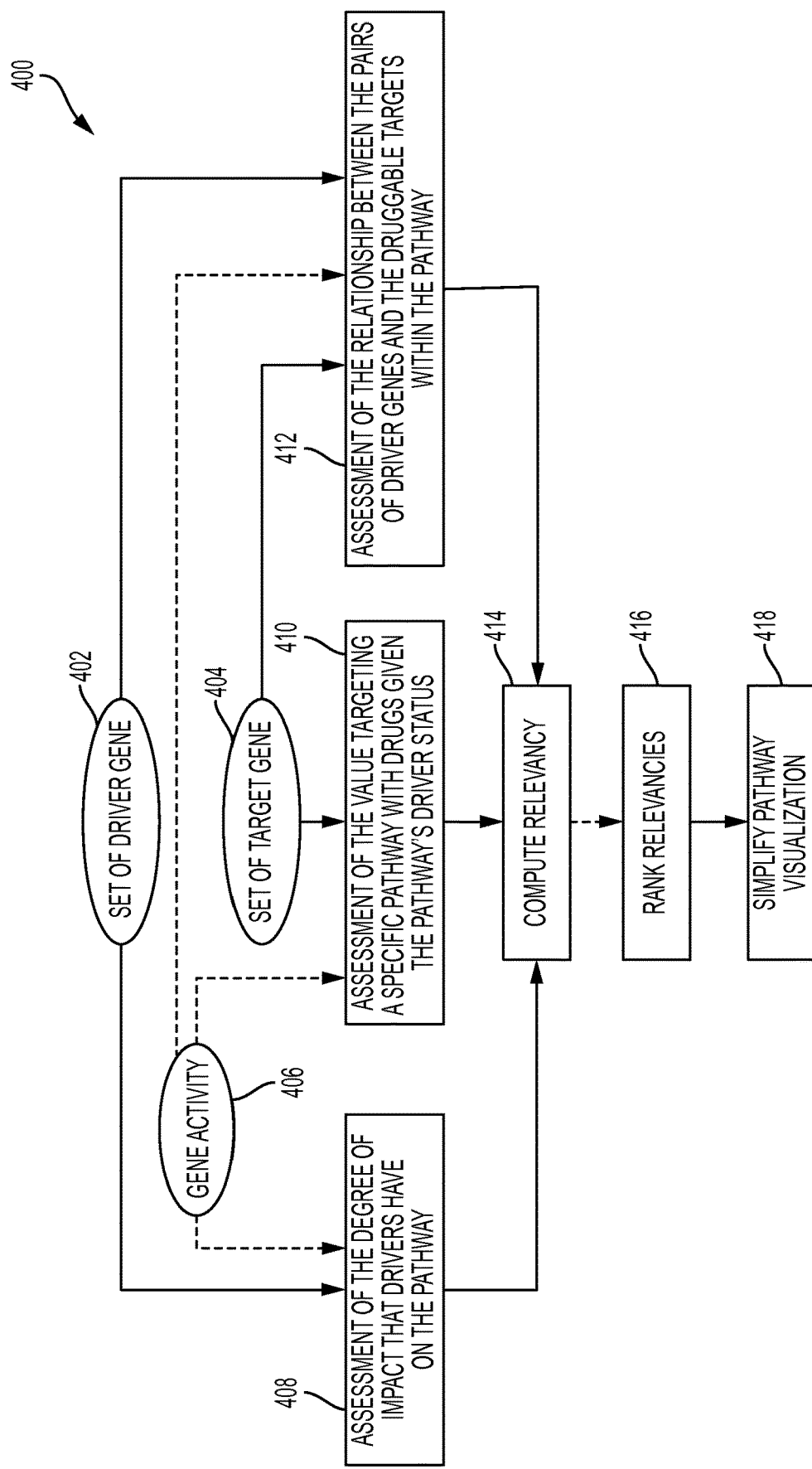
FIG. 4 depicts a flow diagram illustrating a methodology in accordance with one or more embodiments.

FIG. 4 depicts a flow diagram illustrating a methodology 400 of assessment and visualization system 300 in accordance with one or more embodiments. As shown, block 408 receives a set of DG inputs from block 402 and (optionally) gene activity inputs from block 406. Block 408 develops an assessment of the impact that DGs have on the current pathway of interest. An exemplary implementation of block 408 is the A-term calculation shown in FIG. 3B. Block 410 receives (optionally) gene input activity from block 406 and a set of TGs from block 404. Block 410 develops an assessment of the value of targeting a specific pathway with drugs given the pathway's driver status, which includes an alteration of the specific pathway. An exemplary implementation of block 410 is the B-term calculation or the alternative B-term calculation shown in FIG. 3B. Block 412 receives (optionally) gene input activity from block 406, a set of TGs from block 404 and a set of DGs inputs from block 402. An exemplary implementation of block 412 is the C-term calculation shown in FIG. 3B. Block 412 develops an assessment of the relationship between the pairs of DGs and the druggable targets within the pathway. Block 414 takes the outputs of the assessments made by blocks 408, 410 and 412 and determines a relevancy of the current pathway of interest. Block 416 assembles and ranks the relevancies serially determined by block 414. Block 418 simplifies the visualization of pathways ranked by block 416. The rankings identified by blocks 414 and 416 allow the simplification process performed by block 418 to be focused on pathways having the highest relevancy. In addition to the relevance score shown in FIG. 3B, pathway relevancy may be determined by other criteria of the ranked pathways, including but not limited to the number of mutations in the pathway or the number of druggable genes in the pathway. FIG. 5 depicts an exemplary table illustrating how the relevancy rankings identified by blocks 414 and 416 may be organized and displayed. FIGS. 7A, 7B and 8 depict additional details of the pathway visualization simplification process of block 418 and will be described in more detail later in this disclosure.

FIG. 6 depicts diagrams illustrating two examples of how pathway assessments of assessment and visualization system 300 (shown in FIG. 3A) may be implemented in accordance with one or more embodiments. For pathway X, "i" is equal to, sequentially, one (1) to four (4), the second and fourth GMs are not in the pathway that leads to a disease "X," the second and fourth druggable target genes are not upstream or downstream of any druggable gene in the pathway, "a" is one (1) in all cases, "b" is one (1) in all cases, $\partial_{ij}$ is the inverse of the path distance, and $c_{ij}$ is one (1) for the potential pair "i,j." As shown in FIG. 6, the relevance score calculated for pathway X is 0.486.

For pathway Y, "i" is equal to, sequentially, one (1) to four (4), the second and fourth GMs are not in the pathway that leads to a disease "X," the second and fourth druggable target genes are not upstream or downstream of any druggable gene in the pathway, "a" is one (1) in all cases, "b" is one (1) in all cases, $\partial_{ij}$ is the inverse of the path distance, and $c_{ij}$ is one (1) for the potential pair "i,j." Pathway Y is slightly different from pathway X in that the first GM has an addition and more direct pathway to the first druggable gene. As shown in FIG. 6, the relevance score calculated for pathway Y is 0.5, which is higher than the 0.486 relevance score calculated for pathway X. Accordingly, pathway Y is slightly more relevant for the disease of interest than pathway X.

Thus, in assessment and visualization system 300 (shown in FIG. 3A), the A-term, the B-term and the alternative B-term bring into the assessment portion of system 300 a weighting factor that allows a quantification of the importance of a DG or druggable target gene. In addition, the C-term bring into the assessment portion of system 300 a way to take into consideration the actual topology of the current pathway of interest. In other words, the C-term allows a consideration of the connections from the source gene (e.g., GM) to the druggable target. Thus, the weighting applied by the A and B terms is dictated by whether or not there is a path between the DG and target, as well as by the distance of the path between the DG and target. The topology can be further accounted for by including additional information regarding the expression of each gene along that path. In this way, instead of following the path's route along a flat surface (e.g., in a "no gene expression" scenario), the route along a contoured surface may be traced, wherein the contour heights are dictated by the expression level. A score may then be determined to minimize the total distance that accounts for those contours. Additionally, the topology can be accounted for by evaluating the number and variety of possible routes between the DG and the target.

Although the relevancy of a pathway can be established by assessment and visualization system 300, the identified relevant pathway may still be complicated and difficult to visualize. For example, a graph that represents an identified relevant pathway can be comprised of several hundreds of nodes and edges, which make it extremely difficult to find biologically relevant components or to discover new insights. Thus, simplified visualization module 322 (shown in FIG. 3A) and the pathway visualization simplification process of block 418 (shown FIG. 4) provide a framework that simplifies the visualization of a pathway in the context of interactions between nodes from a set of sources to a set of targets. For example, in an investigation into the relationship between a set of proteins that are mutated (due to some conditions) and druggable proteins located downstream of them, the simplified visualization process disclosed herein reduces the amount of visual complexity in the graph to provide immediate visual feedback, and to aid in understanding the biological network and the discovery of new insights.

FIGS. 7A, 7B and 8 depict additional details of simplified visualization module 322 shown in FIG. 3A and the pathway visualization simplification process of block 418 shown in FIG. 4. More specifically, FIGS. 7A and 7B are an NCI-PID pathway model that is used to illustrate an example application of the present disclosure to the ErbB1 downstream signaling pathway, wherein the mutation, or source, is EGFR and the drug targets, or targets, are HGS and PPP2RPA. FIG. 7A shows the original pathway and with the point of intersection, and FIG. 7B shows the revised simplified graph with the pertinent shared intermediate node and the drug targets. In general, intermediate node refers to a node in a path that is not an endpoint. NCI-PID biological pathway models are expert-curated, literature-based biological networks of pathways related to cancer. These pathways are highly detailed with a number of visual features that can be simplified in accordance with the present disclosure for ease of understanding or for non-relevancy with respect to more clinical applications of the data.

To simplify the NCI-PID biological pathway of FIG. 7A, all paths up to length k that connect a source and target were extracted from the original graph. From the resulting subgraph, all relevant entities and functional interactions were then considered for visualization. The entities may include proteins, RNA, small molecules, and complexes. The interactions may include biochemical reactions, complex assemblies, transport, transport with biochemical reactions, template reactions, template reaction regulation, catalysis, and control. Specific features, node types, and interactions can be hidden in the simplified graph of FIG. 7B. For instance, certain small molecules may be hidden to ease visualization, because they may be less relevant to clinicians searching for therapeutic strategies. The process of hiding a node or edge during pathway simplification does not impact the search for paths between the source and target in situations where all nodes will be visited, including as in the illustrated example, small molecules. As part of pathway simplification of the example shown in FIGS. 7A and 7B, small molecules were removed from the network if they only had one (1) input and one (1) output edge and were not part of larger assemblies of molecules. This constraint on removal mitigates the loss, if any, of important mechanism information, such as phosphorylation events that would indicate the activity states of molecules.

Following removal of all specific node types, the graph is then subject to the following additional simplification. In order to determine the nodes and edges that are to be retained and where new edges are to be created, nodes and edges can be evaluated according to different measures of importance. For example, the shortest path between each pair (P) of source (S) and target (T) nodes can be used as a feature of pathway importance and calculated using, for example, Djikstra's Algorithm, the details of which are disclosed a publication written by E. W. Dijkstra, titled "A Note on Two problems in Connection With Graphs", published by Numerische Mathematik 1, pp. 269-271 (1959), the entire disclosure of which is incorporated by reference herein. Thus, nodes (N) will be excluded from the graph based on specific criteria that may be dependent on the output desired. For example, a score for each node may be the frequency a node is visited by P shortest paths. Alternatively, if the source S and target N are kept fixed, the score for each node can be calculated by counting the number of times the node is visited by a path of length k, k+1, k+2, . . . k+N, wherein k is measured based on the number of nodes it traverses, and is the length of the shortest path between S and T.

Nodes visited at least "x" times are kept. This criterion implicitly keeps nodes that are more relevant for the collective set of source-target relationships. A more sophisticated scoring function may be implanted wherein other features are considered, such as the mutual information score of a node's relevancy to the relationship between the source and target. Where a node(s) is excluded, a new edge is created that links the nodes upstream and downstream to the excluded node(s) in the path. In general, an edge refers to a link between two nodes.

A natural extension of the above-described methodology is to continue the exclusion to eliminate all nodes not at branch points of the path, i.e., nodes with only one (1) input edge and one (1) output edge. Nodes having the same name or label are also merged to reduce potential redundancy in the graph, with exceptions applied at the discretion of the user. Moreover, a complex can be also consolidated to the largest complex entirely containing it or to an artificially generated superset complex. In general, a complex is a group of two or more associated proteins, and a superset complex is an entity defined herein as a special complex containing all entities in multiple complexes. Specific features, node types, and interactions can also be removed from the graph. Node merging based on name (specifically the "display name") is performed in all cases where nodes of the same name do not have different localizations specified in the graph. This preserves the potential localization-specific activity of a molecule. Accordingly, applying the above-described simplification operations to the original graph shown in FIG. 7A results in the simplified graph shown in FIG. 7B.

FIG. 8 is a flow diagram depicting additional details an exemplary methodology 800 for carrying out the pathway visualization simplification process of block 418 shown in FIG. 4. As shown in FIG. 8, in methodology 800, block 808 receives a set of DG inputs from block 802, a set of TG inputs from block 804 and (optionally) gene activity input from block 806. Block 808 identifies relevant paths. Block 810 receives the identified relevant paths from block 808 and removes either non-informative and/or non-significant entities. Block 812 receives the output from block 810 and creates simplified relations and relative attributes. The relative attributes of block 812 are information created by the disclosed simplification method to describe the properties of the simplified node or edge (e.g., the distance of synthetic links, the superset complex, etcetera).

Thus it can be seen from the foregoing detailed description that the present disclosure provides a number of technical benefits. In assessment and visualization system 300 (shown in FIG. 3A), the A-term, the B-term and the alternative B-term bring into the assessment portion of system 300 a weighting factor that allows a quantification of the importance of a DG or druggable target gene. In addition, the C-term bring into the assessment portion of system 300 a way to take into consideration the actual topology of the current pathway of interest. In other words, the C-term allows a consideration of the connections from the source gene (e.g., GM) to the druggable target. Thus, the weighting applied by the A and B terms is dictated by whether or not there is a path between the DG and target, and the distance of the path between the DG and target. The topology can be further accounted for by including additional information regarding the expression of each gene along that path. In this way, instead of following the path's route along a flat surface (e.g., in the "no gene expression" scenario), the route along a contoured surface may be traced, wherein the contour heights are dictated by the expression level. A score may then be determined to minimize the total distance that accounts for those contours. Additionally, the topology can be accounted for by looking at the number and variety of possible routes between the DG and the target.

Further technical benefits of the present disclosure include simplified visualization module 322 (shown in FIG. 3A) and the pathway visualization simplification process of block 418 (shown FIG. 4), which provide a framework that simplifies the visualization of a pathway in the context of interactions between nodes from a set of sources to a set of targets. For example, in an investigation into the relationship between a set of proteins that are mutated (due to some conditions) and druggable proteins located downstream of them, the simplified visualization process disclosed herein reduces the amount of visual complexity in the graph to provide immediate visual feedback, and to aid in understanding the biological network and the discovery of new insights. Accordingly, the operation of a computer system implementing one or more of the disclosed embodiments can be improved.

Figure 9:
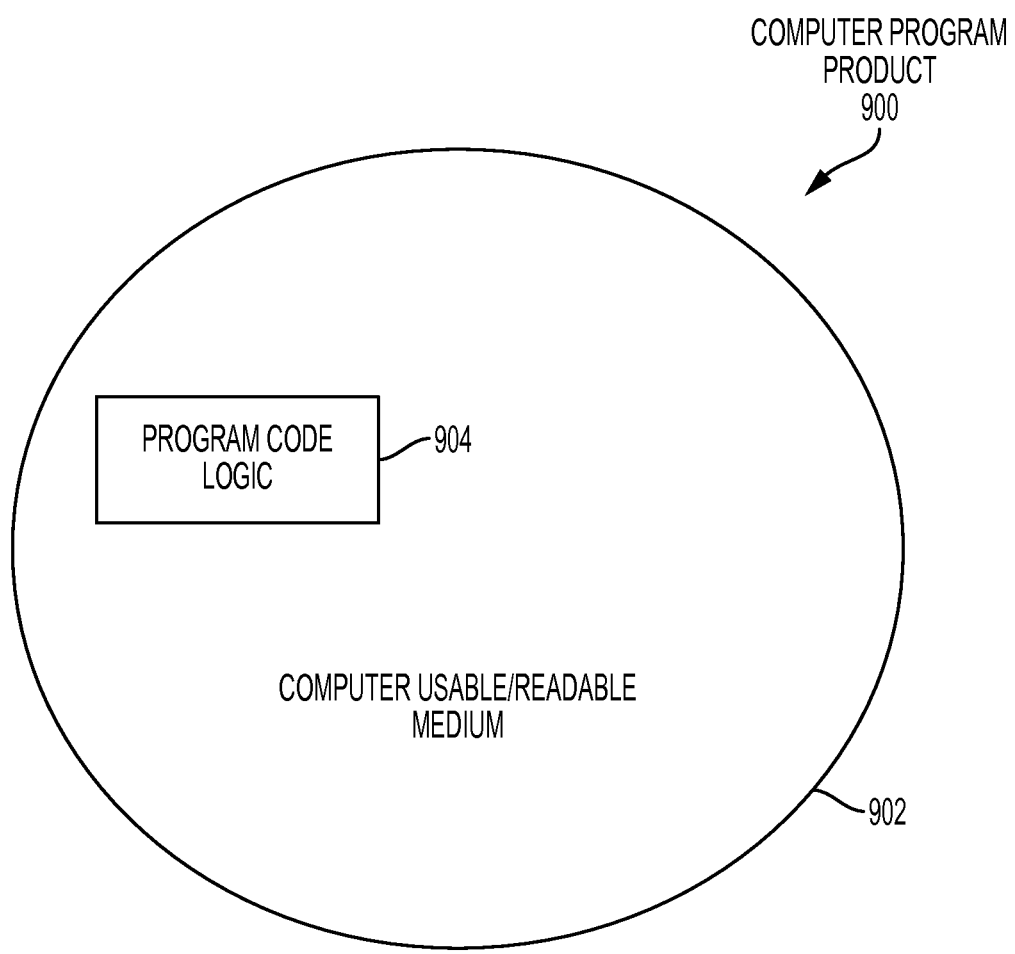
FIG. 9 depicts a computer program product in accordance with one or more embodiments.

Referring now to FIG. 9, a computer program product 900 in accordance with an embodiment that includes a computer readable storage medium 902 and program instructions 904 is generally shown.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will be understood that those skilled in the art, both now and in the future, may make various improvements and enhancements which fall within the scope of the claims which follow.

What is claimed is:

1. A computer implemented method configured to generate a simplified visualization of a relevancy of at least one biological pathway to a disease of interest, the at least one biological pathway having a source gene and a target druggable molecular entity, the method comprising performing multiple iterations of a simplified visualization and relevancy assessment method, wherein one iteration of the multiple iterations of the simplified visualization and relevancy assessment method comprises:

developing, by a processor and stored program instructions, an assessment of an impact of the source gene on the at least one biological pathway;

developing, by said processor and stored program instructions, a value of targeting the at least one biological pathway with a drug of interest, wherein the targeting is based at least in part on an alteration of the at least one biological pathway;

identifying, by said processor and stored program instructions, a relationship between the source gene and the target druggable molecular entity within the at least one biological pathway;

combining:

said assessment of said impact of the source gene on the at least one biological pathway;

said value of the targeting of the at least one biological pathway with a drug of interest; and said relationship between the source gene and the target druggable molecular entity within the at least one biological pathway;

wherein said combining results in an assessment of the relevancy of the at least one biological pathway to the disease of interest;

ranking said assessment of the relevancy of the at least one biological pathway to the disease of interest in comparison with assessments of a relevancy of the at least one biological pathway to the disease of interest that result from others of the multiple iterations of the simplified visualization and relevancy assessment method; and generating the simplified visualization of said at least one biological pathway, wherein the simplified visualization is implemented based at least in part on said ranking of said assessment of the relevancy of the at least one biological pathway to the disease of interest;

wherein generating the simplified visualization comprises:

creating a graph of said at least one biological pathway, wherein said graph comprises a plurality of nodes connected by edges;

identifying relevant paths of said graph;

removing from said relevant paths non-informative or non-significant nodes to create a first subgraph; and simplifying relations and relative attributes of said first subgraph to create a second, simplified subgraph.

2. The computer implemented method of claim 1, wherein said assessment of said impact of the source gene on the at least one biological pathway comprises a weighted value of the source gene.

3. The computer implemented method of claim 1, wherein said value of the targeting of the at least one biological pathway comprises a weighted value of the target druggable molecular entity.

4. The computer implemented method of claim 1, wherein said relationship between the source gene and the target druggable molecular entity within the at least one pathway comprises a topology of said at least one biological pathway from the source gene to the target druggable molecular entity.

5. The computer implemented method of claim 1, wherein said relative attributes of said first graph are used to provide properties of said plurality of nodes or said plurality of edges of said second, simplified subgraph.

* * * * *

UNITED STATES PATENT AND TRADEMARK OFFICE
CERTIFICATE OF CORRECTION

PATENT NO. : 10,534,813 B2
APPLICATION NO. : 14/745616
DATED : January 14, 2020
INVENTOR(S) : Carmeli et al.

It is certified that error appears in the above-identified patent and that said Letters Patent is hereby corrected as shown below:

On the Title Page

Column 1 (72) Inventors: should read as follows:
Boaz Carmeli, Koranit, (IL);
Erhan Bilal, Brooklyn, NY (US);
Takahiko Koyama, Scarsdale, NY (US);
Kahn Rhrissorrakrai, Woodside, NY (US);
Ajay Royyuru, Yorktown Heights, NY (US);
Filippo Utro, White Plains, NY (US);
Zeev Waks, Petach Tikva, (IL)

Signed and Sealed this
Second Day of August, 2022

Katherine Kelly Vidal
*Director of the United States Patent and Trademark Office*